(12) United States Patent
Grumann et al.

(10) Patent No.: US 8,420,807 B2
(45) Date of Patent: Apr. 16, 2013

(54) PROCESS FOR THE PREPARATION OF QUETIAPINE

(75) Inventors: Arne Grumann, Kauniainen (FI); Dzintra Muceniece, Riga (LV); Otto Soidinsalo, Helsinki (FI)

(73) Assignee: Fermion Oy, Espoo (FI)

( * ) Notice: Subject to any disclaimer, the term of this patent is extended or adjusted under 35 U.S.C. 154(b) by 91 days.

(21) Appl. No.: 12/811,536

(22) PCT Filed: Jan. 30, 2009

(86) PCT No.: PCT/FI2009/000021
§ 371 (c)(1),
(2), (4) Date: Dec. 27, 2010

(87) PCT Pub. No.: WO2009/095529
PCT Pub. Date: Aug. 6, 2009

(65) Prior Publication Data
US 2011/0112290 A1    May 12, 2011

Related U.S. Application Data

(60) Provisional application No. 61/024,949, filed on Jan. 31, 2008.

(51) Int. Cl.
*C07D 417/04* (2006.01)
*C07D 281/16* (2006.01)

(52) U.S. Cl.
USPC .................................. 540/551; 544/398

(58) Field of Classification Search ............ 540/551
See application file for complete search history.

(56) References Cited

U.S. PATENT DOCUMENTS

| 3,539,573 A | 11/1970 | Schmutz et al. |
| 4,879,288 A | 11/1989 | Warawa et al. |
| 2006/0063927 A1 | 3/2006 | Etlin et al. |

FOREIGN PATENT DOCUMENTS

| EP | 0 240 228 A1 | 10/1987 |
| EP | 0 282 236 B1 | 9/1988 |
| WO | WO 2005/014590 A2 | 2/2005 |
| WO | WO 2005/028457 A1 | 3/2005 |
| WO | WO 2005/028458 A1 | 3/2005 |
| WO | WO 2005/028459 A1 | 3/2005 |
| WO | WO 2006/094549 A1 | 9/2006 |
| WO | WO 2006/113425 A1 | 10/2006 |
| WO | WO 2006/117700 A2 | 11/2006 |
| WO | WO 2007/004234 A1 | 1/2007 |
| WO | WO 2007/020011 A1 | 2/2007 |

OTHER PUBLICATIONS

International Search Report—dated Jun. 10, 2009 for PCT/FI2009/000021.

*Primary Examiner* — Kahsay T Habte
(74) *Attorney, Agent, or Firm* — Birch, Stewart, Kolasch & Birch, LLP

(57) ABSTRACT

The invention relates to a method for the preparation of 11-(4-[2-(2-hydroxyethoxy)ethyl]-1-piperazinyl]dibenzo [b,f]-1,4-thiazepine and pharmaceutically acceptable salts thereof comprising the reaction of 1-[2-(hydroxyethoxy)-ethyl]piperazine with dibenzo[b,f][1,4]thiazepin-11-ylamine.

14 Claims, No Drawings

PROCESS FOR THE PREPARATION OF QUETIAPINE

CROSS REFERENCE TO RELATED APPLICATIONS:

This application is the National Phase of PCT/FI2009/000021 filed on Jan. 30, 2009 which claims priority under 35 U.S.C 119(e) of U.S. Provisional Application No. 61/024,949 filed on Jan. 31, 2008. The entire contents of the above applications are hereby incorporated by reference into the present application.

FIELD OF THE INVENTION

The present invention provides an economical transamination method for the preparation of 11-(4-[2-(2-hydroxyethoxy)ethyl]-1-piperazinyl)dibenzo[b,f]-1,4-thiazepine of formula I, which is a well established drug substance known under the INN name quetiapine.

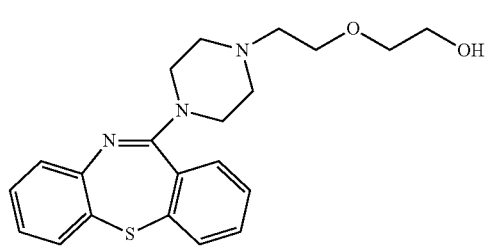

I

It is used as an antipsychotic or neuroleptic, especially in the treatment of schizophrenia. Originator's product Seroquel® contains quetiapine fumarate as an active ingredient.

BACKGROUND OF THE INVENTION

Quetiapine was first described in a patent publication EP 240228 (U.S. Pat. No. 4,879,288). It is prepared starting from dibenzo[b,f][1,4]thiazepin-11-[10H]one of formula II

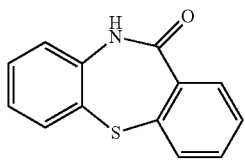

II which is first halogenated with phosphorous oxychloride, then isolated and condensed with 1-(2-hydroxyethoxy) ethyl piperazine to obtain quetiapine. After purification by flash chromatography the yield was 77.7%. As an alternative to halogenation a process via a thioether in the first step is presented.

In the process claimed in EP 282236 the piperazine ring is first condensed with 11-chloro-dibenzo[b,f][1,4]thiazepine and thereafter quetiapine is obtained by its reaction with haloethoxy ethanol. The base is further converted to the hemifumarate salt, which was isolated in 78% yield.

WO 2006/117700 describes a process of EP '228 improved by the destruction of phosphorous oxychloride in situ to decrease the amount of hazardous waste. Phosphorous oxychloride is used only about 1 equivalent to the compound of formula II whereas in the process of EP 240228 it was used in about 15 equivalents.

A reaction of 11-chlorodibenzo[b,f][1,4]thiazepine with a piperazine moiety in the presence of a halide is the improvement described in WO 2006/113425. The process is said to yield quetiapine in high purity.

In WO 2006/094549 there is described a process which avoids the halogenation step and the use of hazardous phosphorous halogenating agents by the reaction of 10H-dibenzo[b,f][1,4]thiazepin-11-one directly with a piperazine derivative. This is achieved by performing the reaction in the presence of titanium alkoxide. Yields of 50-75% as a fumarate salt are reported. Expensive titanium alkoxide is used from about 2 to 3 fold excess to starting compound of formula II.

Also the process of US 2006/0063927 avoids the use of phosphorous compounds in halogenation by using oxalyl chloride as a halogenating agent. The imino chloride is obtained in 66% yield. The reaction of 11-chloro-dibenzo[b,f][1,4]thiazepine with 1-(2-hydroxyethoxy)ethylpiperazine is performed either in the presence of a base in an organic solvent or in a two-phase system. However, the reagent used, oxalyl chloride is poisonous and requires special attention.

A one-pot process for the preparation of quetiapine is described in WO 2007/020011. Phosphorous oxychloride is used in halogenation step about one equivalent to 10H-dibenzo[b,f][1,4]thiazepin-11-one.

WO 2007/004234 describes a process comprising the reaction of chloro ethoxy ethanol with piperazinyl-dibenzo[b,f][1,4]thiazepine dihydrocloride, which is obtained by halogenating the dibenzo[b,f][1,4]thiazepin-11-[10H]one, reacting the imino chloride obtained with piperazine, and treating the obtained compound with an alcoholic solution of hydrogen chloride.

All processes described above use dibenzo[b,f][1,4]thiazepin-11-[10H]one as a starting material. Its preparation requires several steps, and in most cases it has to be even halogenated to the imino chloride before the piperazine moiety can be condensed with it. Halogenating reagents, e.g. phosphorous oxychloride have been used in excess and their removal from the reaction mixture requires evaporation of large amounts.

A different approach using protected intermediates is used e.g. in routes described in WO 2005/014590, WO 2005/028457, WO 2005/028458 and WO 2005/028459. In some cases the reactions may be performed in one pot fashion and no extra purification steps are needed to get a pure product in high yield. However, protection and deprotection steps used lengthen the processes and shorter processes for the preparation of quetiapine are still needed.

SUMMARY OF THE INVENTION

The present invention relates to an economical transamination process for the preparation of quetiapine or salts thereof.

The compounds used in the reactions can be either free bases or their acid addition salts, which both are included unless specifically otherwise mentioned. Accordingly, dibenzo[b,f][1,4]thiazepin-11-ylamine can refer to either free base or its acid addition salt, and similarly 1-[2-(hydroxyethoxy)-ethyl]piperazine can refer to free base or its acid addition salt. However, only either one is used as an acid addition salt in a reaction, not both simultaneously. It is also possible to use starting compounds as free bases and free acid is added separately to the reaction.

It has been discovered that it is possible to produce quetiapine directly by transamination of dibenzo[b,f][1,4]thiazepin-11-ylamine with 1-[2-(hydroxyethoxy)-ethyl]piperazine.

The method comprises the preparation of the compound of formula I or a pharmaceutically acceptable salt thereof

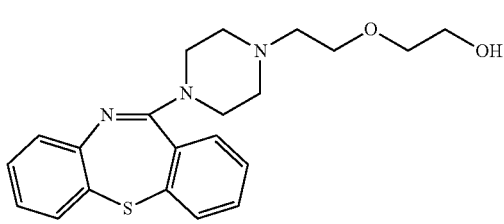

comprising reacting dibenzo[b,f][1,4]thiazepin-11-ylamine of formula III

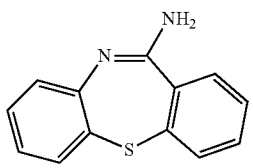

or its acid addition salt with 1-[2-(hydroxyethoxy)-ethyl]piperazine of formula IV

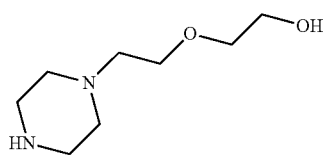

or its acid addition salt and optionally further a reaction of a compound of formula I with a suitable acid to produce a pharmaceutically acceptable salt and isolating the compound of formula I or a salt thereof.

Another aspect of the invention is the method for the preparation of quetiapine by the transamination reaction, further comprising the preparation of the starting material dibenzo[b,f][1,4]thiazepin-11-ylamine or its acid addition salt by the reaction of 2-aminobenzenethiol with a 2-halogenobenzonitrile.

Still another aspect of the present invention is the process for the preparation of quetiapine by the reaction of dibenzo[b,f][1,4]thiazepin-11-ylamine with 1-[2-(hydroxyethoxy)-ethyl]piperazine comprising the recycling of 1-[2-(hydroxyethoxy)-ethyl]piperazine.

One aspect of the present invention is the use of an additional amine in the reaction.

Still another aspect of the present invention is an acid addition salt of dibenzo[b,f][1,4]thiazepin-11-ylamine with an organic or inorganic acid, for example with acetic, fumaric, maleic, oxalic, sulfuric, phosphoric, hydrochloric, hydrobromic or nitric acid.

DISCLOSURE OF THE INVENTION

According to the invention there is provided a process for the preparation of 11-(4-[2-(2-hydroxyethoxy)ethyl]-1-piperazinyl]dibenzo[b,f]-1,4-thiazepine of formula I (quetiapine) or its pharmaceutically acceptable salt. Quetiapine is obtained by transamination of dibenzo[b,f][1,4]thiazepin-11-ylamine with 1-[2-(hydroxyethoxy)-ethyl]piperazine (HEEP). Most of the known processes for the preparation of quetiapine comprise of the displacement of a chloride ion, which is a typical well known process where chloride is a leaving group. Other typical leaving groups are e.g. other halides and sulfonate esters. In this invention the starting material is an amidine of formula III which reacts with the nitrogen of HEEP and the primary nitrogen is exchanged for a tertiary nitrogen. NH2, NHR and NR2 are extremely poor leaving groups and are usually transferred into derivatives such as N-ditosylates or pyridinium salts. However, additional steps are not desirable process wise, and therefore direct transamination was tried. It was surprising to see a clean conversion to the desired product.

1-[2-(hydroxyethoxy)-ethyl]piperazine contains both a secondary nitrogen and an unprotected hydroxy group, both of which may react with dibenzo[b,f][1,4]thiazepin-11-ylamine. Surprisingly the reaction takes place selectively between the secondary nitrogen and the imino carbon, and the protection of the hydroxy group is not needed. The transamination reaction requires at least 1 equivalent of acid for the reaction to proceed. The acid can be introduced to the reaction by using an acid addition salt of either of the starting compounds or free acid can be added to the reaction mixture.

Dibenzo[b,f][1,4]thiazepin-11-ylamine may be used as a suitable acid addition salt such as its HCl salt. Other suitable salts are e.g. salts with acetic, fumaric, maleic, oxalic, sulfuric, phosphoric, hydrobromic or nitric acid.

Alternatively, dibenzo[b,f][1,4]thiazepin-11-ylamine may be used as a base, and 1-[2-(hydroxyethoxy)-ethyl]piperazine (HEEP) may be used as an acid addition salt. Preferably HEEP is used as a free base, and dibenzo[b,f][1,4]thiazepin-11-ylamine is used as a salt.

In case HEEP is used in large excess it is possible to recycle the unreacted amount. HEEP can be used in 1 to 10 equivalents to the starting compound of formula III e.g. 1.5 to 8 equivalents or even 2 to 4 equivalents is suitable.

The amount of HEEP can be reduced by the use of an appropriate additional amine, such as N,N-dimethylcyclohexylamine, N,N-dimethyl aniline, tributylamine or 2,4,6-trimethylpyridine. The additional amine may be used about 0 to 10 equivalents to dibenzo[b,f][1,4]thiazepin-11-ylamine, for example about 1 to 2 equivalents is suitable. In one embodiment of the invention the transamination reaction may be performed in a suitable organic solvent, e.g. in dimethyl formamide (DMF), dimethyl sulphoxide (DMSO), or 1-methyl-2-pyrrolidinone (NMP). In another embodiment of the invention HEEP may act as a solvent in the reaction. Reaction of dibenzo[b,f][1,4]thiazepin-11-ylamine hydrochloride with 2 to 4 equivalents of 1-[2-(hydroxyethoxy)-ethyl]piperazine (HEEP) in the presence of an additional amine and without any additional solvent is the preferred method.

The temperature of the reaction depends on the solvent used. If no additional solvent is used, the temperature between about 100-200° C. may be used, e.g. the temperature about 140-180° C. is suitable. The reaction time depends on the temperature used and it may be e.g. from 2 to 70 hours.

The starting material of the process, dibenzo[b,f][1,4]thiazepin-11-ylamine, can be made e.g. as described in J. Heterocyclic Chem., 34 (1997), 465-467, by treating 2-aminobenzenethiol with 2-fluorobenzonitrile. The process can be performed in one-pot or the intermediate aminocyanodiphenylsulfide can be isolated. The process described comprises the reaction of 2-aminobenzenethiol with 2-fluorobenzonitrile in dimethylformamide (DMF) in the presence of sodium hydride at 0° C. in nitrogen atmosphere. Isolated 2-aminophenyl 2'-cyanophenyl sulfide is transferred to dibenzo[b,f][1,4]thiazepin-11-ylamine in tetrahydrofuran with sodium hydride.

Other methods for the preparation of dibenzo[b,f][1,4]thiazepin-11-ylamine include e.g. the use of $K_2CO_3$ in the first step and potassium or sodium tert-butoxide (tBuOK or tBuONa) in the second step to avoid the use of sodium hydride all together. Also other halogenobenzonitriles like 2-chloro-, 2-bromo- or 2-iodobenzonitrile can be used as starting materials. In addition the first two steps and further the formation of the acid addition salt can be perfomed in a one-pot fashion using dimethylformamide, tetrahydrofuran, toluene or a mixture thereof as a solvent.

After the reaction of dibenzo[b,f][1,4]thiazepin-11-ylamine hydrochloride with 1-[2-(hydroxyethoxy)-ethyl]piperazine quetiapine may be isolated from the reaction mixture e.g. by extraction after the addition of water. Extraction solvents used may be e.g. hot toluene, xylene or dichloromethane. Excess of HEEP will remain in the water phase and it can be isolated by evaporation of water and purified by distillation. Another possibility is to add an inorganic base such as potassium carbonate to the aqueous phase and crude HEEP will separate. Separated HEEP can be further purified by distillation.

In case an additional amine has been used it can be removed as its acid addition salt or with acidic water washes. Quetiapine may be isolated from the reaction mixture as a free base or it can be converted directly to its hemifumarate salt or first to a different addition salt, which is further liberated and converted to the hemifumarate and isolated.

The methods of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants, products and catalyst.

The invention will be further clarified by the following nonlimiting examples, which are intended to be purely exemplary of the invention.

EXAMPLES

Example 1

2-Amino-2'-cyanodiphenylsulfide

2-Aminobenzenethiol (11 ml) dissolved in dimethylformamide (DMF) (25 ml) was added drop wise to a suspension of $K_2CO_3$ (13.8 g) in DMF (90 ml) with stirring under argon. The reaction mixture was warmed up and stirred at 80-90° C. for 1 h. Then a solution of chlorobenzonitrile (13.7 g) in DMF (25 ml) was added drop wise and stirring was continued for 4 h at 90° C. After the reaction was complete the mixture was poured into ice water and extracted with ethyl acetate (250+ 3×150 ml). The combined organic phases were dried with sat. NaCl solution (3×100 ml), treated with activated carbon and evaporated to dryness. The residue afforded a solid (20.05 g, 89%) upon cooling to 4° C. over night. M.p. 89-90° C.

Example 2

Dibenzo[b,f][1,4]thiazepin-11-ylamine

2-Amino-2'-cyanodiphenylsulfide (4.5 g) dissolved in anhydrous tetrahydrofuran (THF) (60 ml) and NaH (1.193 g, 60% dispersion in oil) were refluxed with stirring under argon for 2 h. The reaction mixture was diluted with water (20 ml) and extracted with ethyl acetate (4×25 ml). The combined organic phases were dried with $Na_2SO_4$ and evaporated to dryness to obtain dibenzo[b,f][1,4]thiazepin-11-ylamine (3.68 g, 82%) which could be used without purification.
M.p. 180-181° C.

Example 3

Dibenzo[b,f][1,4]thiazepin-11-ylamine hydrochloride

A solution of gaseous HCl in i-PrOH (5.7 g, 31 wt-%) was added dropwise under stirring to a solution of dibenzo[b,f][1,4]thiazepin-11-ylamine (10.6 g) dissolved in a isopropanol/tert-butyl methyl ether (TBME) mixture (150 ml/120 ml). Stirring was continued for 1 h and the formed precipitate was filtered off, washed with tert-butyl methyl ether (TBME) and dried on air to obtain the desired compound as a colorless solid (11.2 g, 91%).
M.p. 279-282° C.

Example 4

2-[2-(4-Dibenzo[b,f][1,4]thiazepin-11-yl-piperazin-1-yl)ethoxy]ethanol hemifumarate Dibenzo[b,f][1,4]thiazepin-11-ylamine hydrochloride (80.0 g, assay 99+%), 1-[2-(hydroxyethoxy)-ethyl]piperazine (HEEP, 111.0 g) and N,N-dimethylcyclohexylamine (DMCHA, 58.1 g) were heated with stirring at 155° C. for 58 h.

The reaction mixture was cooled to room temperature.

30 grams of reaction mixture was taken in a flask and dissolved in dichloromethane (60 ml) and washed twice with water (30 ml). Concentrated HCl (2.0 g) was added with water (30 ml) and refluxed (30 min). The phases formed were separated and concentrated HCl (10.0 g) was added to the organic phase. After refluxing for 30 minutes water (60 ml) was added and the mixture was refluxed again for 30 minutes. After phase separation the aqueous phase pH was adjusted to 13-14 with 50% NaOH (7.48 g) and toluene (60 ml) was added. After extraction and phase separation (70° C./15 min) the organic phase was washed with water (30 ml) and evaporated to dryness. The residue was (16.24 g, thick oil) dissolved in 80% ethanol (71 ml) and fumaric acid (2.45 g) was added. The mixture was warmed up (78° C./10 minutes) and cooled gradually to 0° C. White crystals formed were filtered, washed with cold ethanol (10 ml) and dried to obtain 12.17 g (74% yield) of quetiapine hemifumarate.

Example 5

2-[2-(4-Dibenzo[b,f][1,4]thiazepin-11-yl-piperazin-1-yl)ethoxy]ethanol

A. With isolation of 1-[2-(hydroxyethoxy)-ethyl]piperazine (HEEP) by distillation Dibenzo[b,f][1,4]thiazepin-11-ylamine hydrochloride (25.0 g, assay 99+%) and 1-[2-(hydroxyethoxy)-ethyl]piperazine (HEEP) (116.0 g) were heated with stirring at 173-175° C. for 5 h in a continuous slow flow of argon.

The reaction mixture was cooled to room temperature and diluted with water (465 ml). After $K_2CO_3$ (6.56 g) was added it was warmed to 70° C. and extracted two times with hot (70-75° C.) toluene.

The combined organic phases were evaporated to dryness under reduced pressure to obtain 35.1 g of thick oil. Fumaric acid (4.78 g) dissolved in hot isopropanol (85 ml) was added to the oil dissolved in hot isopropanol (85 ml). The mixture was cooled to room temperature and left at 4° C. overnight. The solid formed was filtered off and dried to obtain 34.40 g (assay 97%, yield 79%) of quetiapine hemifumarate. Re-crystallization from isopropanol (1.4 L) afforded 30.7 g (assay 99%, recovery 91%) of quetiapine hemifumarate.

M.p. 172-173° C.

The aqueous phase was reduced in volume (~80%) by evaporation of water under reduced pressure (60° C./60 mbar). The residue was distilled at room temperature and 10 mbar after the rest of water was removed. Two fractions of 1-[2-(hydroxyethoxy)-ethyl]piperazine (HEEP) were collected: at 168-170° C./20 mbar (15.88 g) and 174° C./25 mbar (74.68 g). The total recovery of HEEP was 90%.

B. With Isolation of HEEP Using Phase Separation and Distillation

Dibenzo[b,f][1,4]thiazepin-11-ylamine hydrochloride (15.0 g, assay 99%) and 1-[2-(hydroxyethoxy)-ethyl]piperazine (HEEP) (70.0 g) were heated with stirring at 172-176° C. for 5 h under continuous slow flow of argon.

The reaction mixture was cooled to room temperature and diluted with water (180 ml). The resulting mixture was warmed to 65° C. and extracted three times with hot toluene (110, 60 and 60 ml).

The combined organic phases were evaporated to dryness under reduced pressure to obtain 22.4 g of thick oil. The oil was dissolved into hot isopropanol (50 ml) and fumaric acid (3.05 g) dissolved in hot isopropanol (60 ml) was added. The mixture was cooled to room temperature and left at 4° C. overnight. The solid formed was filtered off and dried to obtain 21.95 g of quetiapine hemifumarate (yield 83%, assay 95%). Crystallization from isopropanol (~1.4 L) afforded 20.7 g of quetiapine hemifumarate (recovery 95%, assay 98%).

M.p. 172-174° C.

Solid $K_2CO_3$ (90 g) was added to the aqueous phase with stirring. The temperature of the solution increased to 50° C. and crude HEEP as an upper layer was formed. It was separated and purified by distillation. Water was removed under reduced pressure (10 mbar at room temperature) and HEEP was distilled under reduced pressure (134-136° C./4 mbar) to give a colourless liquid (50.89 g, assay 99.3%).

What is claimed is:

1. A method for the preparation of the compound of formula I or a pharmaceutically acceptable salt thereof

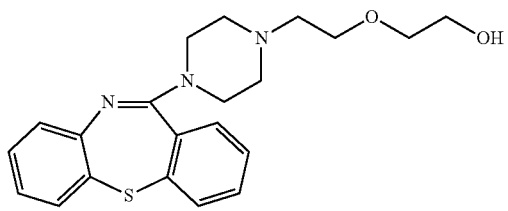

comprising:
reacting dibenzo[b,f][1,4]thiazepin-11-ylamine of formula III

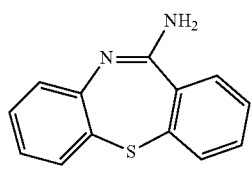

or its acid addition salt, wherein the acid addition salt is formed with an acid selected from the group consisting of acetic, fumaric, maleic, oxalic, sulfuric, phosphoric, hydrochloric, hydrobromic and nitric acid,
with 1-[2-(hydroxyethoxy)-ethyl]piperazine of formula IV

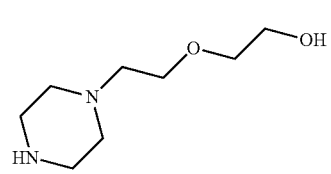

or its acid addition salt and
wherein the compound of formula III and the compound of formula IV are not both acid addition salts and wherein an acid is added to the reaction mixture of the compound of formula III and the compound of formula IV if both the compound of formula III and the compound of formula IV are free bases;
optionally liberating the salt of the compound of formula I with a base:
optionally further reacting a compound of formula I with a pharmaceutically acceptable acid to produce a pharmaceutically acceptable salt; and
isolating the compound of formula I or a salt thereof.

2. A method of claim 1, wherein the acid addition salt of a compound of formula III with sulfuric or hydrochloric acid is used.

3. The method of claim 1, further comprising the preparation of the compound of formula III comprising the reaction of 2-aminobenzenethiol with a 2-halogenobenzonitrile.

4. The method of claim 3 wherein the 2-halogenobenzonitrile is 2-chlorobenzonitrile or 2-bromobenzonitrile or 2-iodobenzonitrile or 2-fluorobenzonitrile.

5. The method of claim 3 wherein the 2-halogenobzonitrile is 2-chlorobenzonitrile.

6. The method of claim 1, wherein the reagent 1-[2-(hydroxyethoxy)-ethyl]-piperazine is used in 1 to 10 equivalents to the starting compound dibenzo[b,f][1,4]thiazepin-11-ylamine.

7. The method of claim 1, wherein the reagent 1-[2-(hydroxyethoxy)-ethyl]-piperazine is used in 1.5 to 8 equivalents to the starting compound dibenzo[b,f]thiazepin-11-ylamine.

8. The method of claim 1, wherein the reagent 1[2-(hydroxyethoxy)-ethyl]-piperazine is used in 2 to 4 equivalents to the starting compound dibenzo[b,f][1,4]thiazepin-11-ylamine.

9. The method of claim 1 wherein no additional solvent is used.

10. The method of claim 1 further comprising the use of an additional amine in the reaction;
wherein the additional amine used is N,N-dimethylcyclohexylamine, N,N-dimethyl aniline, tributylamine or 2,4,6-trimethylpyridine.

11. The method of claim 10, wherein the additional amine used is N,N-dimethylcyclohexylamine.

12. The method of claim 1 further comprising the recycling of 1[2-(hydroxyethoxy)ethyl]piperazine.

13. The method of claim 12 wherein quetiapine is extracted from the reaction mixture and the excess 1-[2-(hydroxyethoxy)-ethyl]piperazine remaining in the water phase is isolated by evaporation of water and purified by distillation.

14. The method of claim 12 wherein quetiapine is extracted from the reaction mixture and the excess of 1-[2-(hydroxyethoxy)-ethyl]piperazine remaining in the water phase is isolated by addition of an inorganic base and phase separation followed by distillation.

* * * * *